United States Patent [19]

DeLuca et al.

[11] 4,367,177
[45] Jan. 4, 1983

[54] PROCESS FOR PREPARING 23,25-DIHYDROXYVITAMIN $D_3$

[75] Inventors: Hector F. DeLuca; Heinrich K. Schnoes; Joseph K. Wichman, all of Madison, Wis.

[73] Assignee: Wisconsin Alumni Research Foundation, Madison, Wis.

[21] Appl. No.: 254,570

[22] Filed: Apr. 15, 1981

[51] Int. Cl.$^3$ .............................................. C07J 9/00
[52] U.S. Cl. .................................................. 260/397.2
[58] Field of Search ...................................... 260/397.2

[56] References Cited

U.S. PATENT DOCUMENTS 4,119,647 10/1978 Liebman et al. ................. 260/397.2
4,279,826 7/1981 DeLuca et al. .................. 260/397.2

Primary Examiner—Elbert L. Roberts
Attorney, Agent, or Firm—Howard W. Bremer

[57] ABSTRACT

A process for preparing 23,25-dihydroxyvitamin D compounds and hydroxy-protected derivatives thereof, and novel intermediates used in the process, are provided.

12 Claims, No Drawings

PROCESS FOR PREPARING 23,25-DIHYDROXYVITAMIN $D_3$

The invention described herein was made in the course of work under a grant or award from the Department of Health and Human Services.

This invention relates to a process for the preparation of vitamin D compounds. More specifically, this invention relates to the preparation of side chain-dihydroxylated vitamin D metabolites.

It is well known that the action of the D vitamins (e.g. vitamin $D_3$ or $D_2$) in regulating calcium and phosphorus, homeostasis in the animal or human requires prior metabolism, in vivo, to hydroxylated forms. Several hydroxylated metabolites have been found to occur naturally, including, for example, 25-hydroxyvitamin $D_3$ and 25-hydroxyvitamin $D_2$ as well as sidechain-dihydroxylated forms, namely 24,25-dihydroxyvitamin $D_3$ and 25,26-dihydroxyvitamin $D_3$. All of these compounds exhibit vitamin D-like biological activity in vivo, being effective for example in stimulating intestinal calcium transport and bone mineral mobilization. Recently another related dihydroxy metabolite of vitamin $D_3$ has been discovered and characterized as 23,25-dihydroxyvitamin $D_3$ by DeLuca et al. (co-pending U.S. Patent application Ser. No. 189,481, filed Sept. 22, 1980).

A convenient process for the chemical synthesis of this novel vitamin D metabolite and of related compounds has now been developed.

The starting material for this process is a keto-steroid of general structure I shown below,

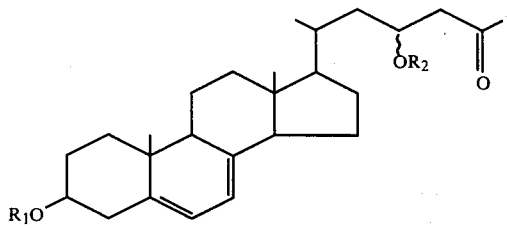

where each of $R_1$ and $R_2$ is selected from the group consisting of hydrogen, acyl and alkylsilyl and where the substituent at carbon 23 has the stereoconfiguration as is desired in the vitamin product.

As used in this specification and the claims the word "acyl" denotes an aliphatic acyl group of 1 to 5 carbons, such as acetyl, propionyl, butyryl, pentoyl and the isomeric forms thereof, or an aromatic acyl group, such as benzoyl, or the halo- or nitro-benzoyls. The word "alkyl" denotes an alkyl group of 1 to 5 carbons such as methyl, ethyl, propyl, butyl, pentyl and the isomeric forms thereof.

The keto steroid of structure I, above, where $R_1$ and $R_2$ is hydrogen, is available according to the procedure of Wichmann et al., *Tetrahedron Letters*, 21, p. 4667–4670 (1980), and the corresponding hydroxy-protected derivatives (e.g. acyl or alkylsilyl derivatives) are readily prepared from this material. Thus, treatment of the dihydroxy compound with acetic anhydride in pyridine gives the 3,23-diacetate. Other derivatives such as, for example, the dibenzoate or di-trimethylsilyl ether derivative are available by analogous methods well known in the art. All of these derivatives are suitable for the subsequent steps of the process, hydroxy-protection for such use not being required.

Treatment of the 25-keto-starting material with methyl Grignard reagent (e.g., methyl magnesium bromide) or with methyl lithium in a suitable solvent (e.g. diethyl ether, tetrahydrofuran) yields the trihydroxysteroid of general structure II shown below

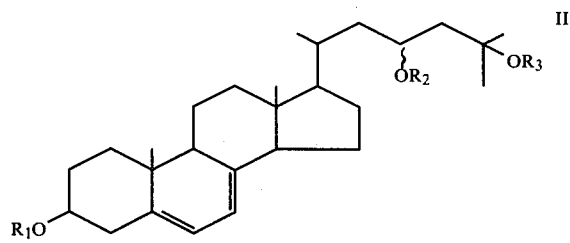

During this Grignard or methyl lithium reaction step and subsequent workup, hydroxy protecting groups that may have been present in the starting material (e.g. acyl, alkylsilyl) would normally be removed to yield product II above where $R_1$, $R_2$ and $R_3$ are hydrogen. If desired, the hydroxy groups may be reprotected, e.g. by acylation or alkylsilylation according to the standard methods to yield the corresponding partially or completely hydroxy-protected product of structure II shown above, where each of $R_1$, $R_2$, and $R_3$ is selected from hydrogen, acyl or alkylsilyl. For example, treatment of the trihydroxy product with acetic anhydride at room temperature in pyridine yields the 3,23-diacetyl compound, whereas at elevated temperatures (75°–100° C.) the 3,23,25-triacetyl derivative is obtained. By analogous methods fully or partially hydroxy-protected derivatives (e.g., derivatives carrying other acyl groups, such as benzoyl, or alkylsilyl protecting groups) are obtained. A partially acylated derivative (e.g., 3,23-diacyl) may also be further acylated (e.g., at C-25) by a different acyl group, or may be alkylsilylated to obtain derivatives carrying mixed hydroxy-protecting functions, and selective removal of protecting groups is also readily accomplished, e.g., selective hydrolysis (10% KOH/MeOH, room temperature) of a 3,23,25-tri-O-acyl derivative to yield the 3,23-dihydroxy-25-O-acyl compound. Different protecting groups can then be introduced at the free hydroxy-positions, and it is thus obvious that combination of selective protection/deprotection steps will yield derivatives with any desired combination of hydroxy protecting groups in the product. Hydroxy protection is, however, not required for the subsequent conversions.

Ultra-violet irradiation of the above 5,7-diene intermediate, II, in a suitable solvent (e.g. aliphatic or aromatic hydrocarbon, ethanol, methanol, ether) yields the corresponding previtamin derivative of the general structure III shown below

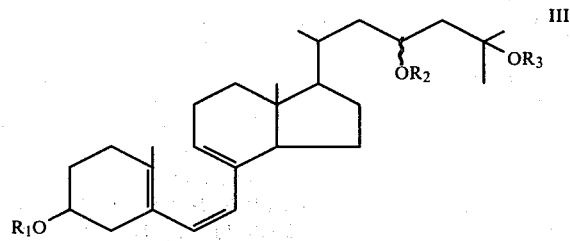

where each of $R_1$, $R_2$ and $R_3$ is selected for the group consisting of hydrogen, acyl, and alkylsilyl.

This previtamin D intermediate is allowed to stand in solution at room temperature or slightly elevated temperature for a prolonged time (e.g. several days) or, preferably, is subjected to brief heating (50°–80° C.) in a suitable solvent (e.g. alcoholic solvent, ether, benzene or aliphatic hydrocarbon solvent) to yield the desired vitamin D compound of general structure IV below

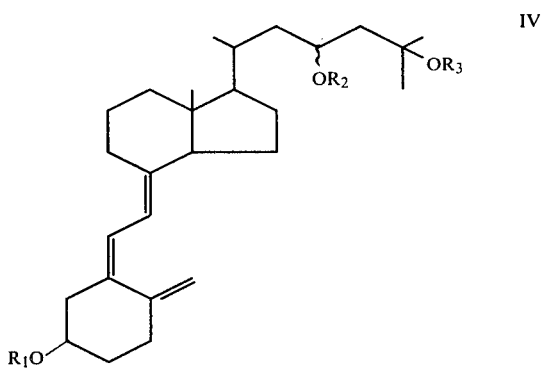

IV where each of $R_1$, $R_2$ and $R_3$ is selected from the group of hydrogen, acyl, and alkylsilyl.

If hydroxy protecting groups are present, these may be removed according to standard procedures (e.g. heating in 5% methanolic base for ca. 2 hr, or treatment with a hydride reagent, for removal of acyl groups, or treatment of an alcoholic solution of the compound with very dilute acid at room temperature for removal of alkylsilyl groups) to obtain the corresponding free hydroxy-compound, 23,25-dihydroxyvitamin $D_3$, represented by structure IV above, where $R_1$, $R_2$ and $R_3$ are hydrogen.

The invention is further described by the following specific examples, which illustrate a typical preparation, but are not to be construed as limiting the appended claims.

EXAMPLE 1

27-nor-23-hydroxy-25-keto-cholesta-5,7-diene was prepared as a mixture of the two possible C-23 epimers according to the procedure of Wichmann et al., in *Tetrahedron Letters* 21, 4667–4670 (1980). These epimers were separated as described in the above reference to yield, in pure form, each of the two epimers, designated here for convenience, isomer A and isomer B, respectively.

Isomer A (5 mg) dissolved in 5 ml of diethylether was treated with a 10-fold excess of methyl magnesium bromide. The mixture was stirred at room temperature for 15 min, then treated with 25 ml of 1 N HCl and extracted with $CH_2Cl_2$; the extracts were washed with dilute bicarbonate and saturated NaCl-solutions, and after evaporation of solvents, the product was purified on high-performance liquid chromatography (HPLC), using a μ-Porasil column (0.79 × 30 cm; Waters Associates, Milford, MA) and 3.5% isopropanol in $CH_2Cl_2$ as eluting solvent, to yield 2.4 mg of cholesta-5,7-diene-3β,23,25-triol-isomer A, eluting at about 39 ml, exhibiting the following mass spectrum: m/e 416, 100% $M^+$; 398, 10%, $M^+$-$H_2O$; 383, 60%, $M^+$-$H_2O$-$CH_3$; 357, 21%, $M^+$-$C_3H_7O$; 342, 23% $M^+$-$C_3H_7O$-$CH_3$; 271, 31%, $M^+$-side chain; 143, 83%, $C_{11}H_{11}^+$.

A portion of this product (0.5 mg) was irradiated for 15 min in 150 ml of 20% benzene in diethyl ether using a quartz immersion well and a Hanovia-608A36 lamp fitted with a Corex filter. After solvent evaporation, the desired previtamin D product (23,25-dihydroxy previtamin $D_3$-isomer A) was purified by HPLC (0.62 cm × 25 cm column of Zorbax-SIL, Dupont, Inc., Wilmington, Del.) eluted with 3.5% isopropyl alcohol in $CH_2Cl_2$. The previtamin product elutes at ca. 51 ml in this system.

This previtamin D-product, dissolved in 2 ml of ethanol, was heated to 70° C. for 2.5 hours, to effect the conversion of the previtamin to the vitamin carbon skeleton. Purification by HPLC (0.62 × 25 cm, Zorbax-Sil) eluted with 4% isopropyl alcohol in $CH_2Cl_2$ gave 0.24 mg of 23,25-dihydroxyvitamin $D_3$-isomer A, collected at 28 ml, and exhibiting the following spectral properties: UV $\lambda_{max}$ 265 nm, $\lambda_{min}$ 228 nm; mass spectrum, m/e 416.3319 (calculated, $M^+$ = 416.3290) 27%, $M^+$; 398, 2.5%, $M^+$-$H_2O$; 383, 13%, $M^+$-$H_2O$-$CH_3$; 271, 8.5%, $M^+$-side chain; 253, 9.7%, 271-$H_2O$; 136, 100%, ring A+C6, C7; 118, 136-$H_2O$; NMR ($CDCl_3$), δ6.23, d, J=11 Hz, C-6; 6.03, d, J=11 Hz, C-7; 5.05, m, C-19(E); 4.81, m, C-19(Z); 4.13, m, C-23; 3.94, m, C-3; 1.33, s, C-26; 1.26, s, C-27; 1.00, d, J=7 Hz, C-21; 0.58, s, C-18;

EXAMPLE 2

A solution of 5 mg of 27-nor-23-hydroxy-25-keto-cholesta-5,7-diene, isomer B, obtained as described in Example 1 above, was treated with methyl magnesium bromide using the conditions described in Example 1, and after HPLC purification of the resulting product using the conditions described in Example 1, 1.2 mg of cholesta-5,7-diene-3β,23,25-triol, isomer B, was obtained (eluting at ca 58 ml on HPLC) exhibiting a mass spectrum with m/e 416, 83%, $M^+$; 398, 11%, $M^+$-$H_2O$; 383, 80%, $M^+$-$H_2O$-$CH_3$; 357, 33%, $M^+$-$C_3H_7O$; 342, 22%, 357-$H_2O$; 271, 23%, $M^+$-side chain; 143, 100%, $C_{11}H_{11}^+$.

About 0.5 mg of this product was irradiated using the experimental conditions of Example 1 to give 23,25-dihydroxyprevitamin $D_3$, isomer B, which was purified by HPLC using a 0.79 × 30 cm μPorasil column, eluted with 7% of 2-propanol in hexane. The desired previtamin was collected at ca 38 ml, and then subjected to thermal isomerization (heating in ethanol solution to 70° C. for 2.5 hrs, as described above). Subsequent purification of the resulting product on HPLC, using a 0.62×23 cm Zorbax-Sil column, and 7% 2-propanol in hexane as eluant, gave at ca. 35 ml elution volume, the desired 23,25-dihydroxyvitamin $D_3$, isomer B, with the following spectral properties: UV, $\lambda_{max}$ 265 nm; $\lambda_{min}$ 228 nm; mass spectrum, m/e 416.3273 (calculated, 416.3290), 18%, $M^+$; 398, 2%, M-$H_2O$; 383, 10%, $M^+$-$H_2O$-$CH_3$; 271, 7%, $M^+$-side chain; 253, 8%, 271-$H_2O$; 136, 100%, A ring+C6 and C7; 118, 97%, 136-$H_2O$; NMR ($CDCl_3$) δ6.23, d, J=10.5 Hz, C-6; 6.03, d, J=10.5 Hz, C-7; 5.05, m, C-19(E); 4.82, m, C-19(Z); 4.10, m, C-23; 3.95, m, C-3; 1.32, s, C-26; 1.28, s, C-27; 0.98, d, J=6 Hz, C-21; 0.56, s, C-18. This compound is chromatographically and spectrally identical with the natural product, as obtained from chick kidney homogenates as described by DeLuca et al. in co-pending U.S. patent application, Ser. No. 189,481.

From the foregoing it is evident also that ketosteroid of general structure I comprising a mixture of both possible C-23-stereoisomers (epimeric mixture) can be subjected to process steps of this specification, whereby an epimeric mixture of the vitamin product of general structure IV is obtained, from which, if desired, the two C-23-epimers are obtained in pure form by chromatographic separation (e.g. hplc on Zorbax-Sil, using 5% 2-propanol in hexane as eluting solvent).

We claim:

1. A compound of the formula

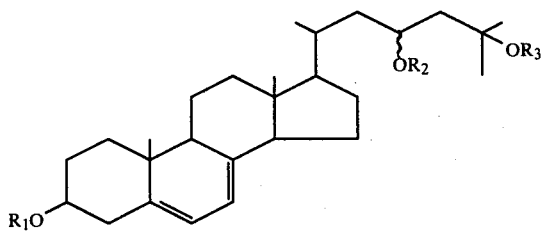

wherein each of $R_1$, $R_2$, and $R_3$ is selected from the group consisting of hydrogen, acyl, and alkylsilyl.

2. A compound according to claim 1 wherein each of $R_1$, $R_2$ and $R_3$ is selected from the group consisting of acetyl and benzoyl.

3. Cholesta-5,7-diene-3β,23,25-triol.

4. The compound of claim 3, having the R configuration at carbon 23.

5. The compound of claim 3, having the S configuration at carbon 23.

6. A compound of the formula

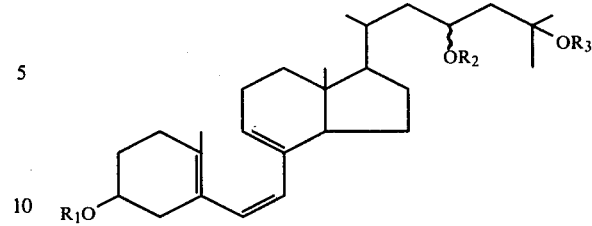

wherein each of $R_1$, $R_2$ and $R_3$ is selected from the group consisting of hydrogen, acyl, and alkylsilyl.

7. A compound according to claim 6 wherein each of $R_1$, $R_2$, and $R_3$ is hydrogen.

8. A compound according to claim 6 wherein each of $R_1$, $R_2$ and $R_3$ is selected from the group consisting of acetyl and benzoyl.

9. A compound of the formula

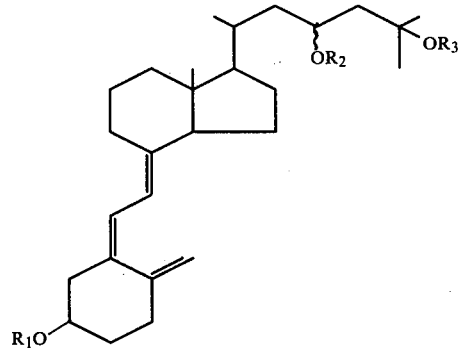

wherein each of $R_1$, $R_2$, and $R_3$ is selected from the group consisting of hydrogen and alkylsilyl, with the proviso that when the substituent at carbon 23 has the steric configuration as it exists in the natural metabolite, all of $R_1$, $R_2$ and $R_3$ cannot be hydrogen.

10. A compound according to claim 9 wherein each of $R_1$, $R_2$, and $R_3$ is alkylsilyl.

11. A compound according to claim 10, wherein the substituent of carbon 23 has the (R)-configuration.

12. A compound according to claim 10 wherein the substituent of carbon 23 has the (S)-configuration.

* * * * *